(12) United States Patent
Rogers

(10) Patent No.: US 9,101,509 B2
(45) Date of Patent: Aug. 11, 2015

(54) PROTECTIVE LIMB WRAP

(71) Applicant: Robert Rogers, Bluffs, IL (US)

(72) Inventor: Robert Rogers, Bluffs, IL (US)

( * ) Notice: Subject to any disclaimer, the term of this patent is extended or adjusted under 35 U.S.C. 154(b) by 0 days.

(21) Appl. No.: 14/313,286

(22) Filed: Jun. 24, 2014

(65) Prior Publication Data

US 2015/0119774 A1 Apr. 30, 2015

Related U.S. Application Data

(60) Provisional application No. 61/896,974, filed on Oct. 29, 2013.

(51) Int. Cl.
| | |
|---|---|
| *A61F 5/00* | (2006.01) |
| *A61F 13/00* | (2006.01) |
| *A61F 15/00* | (2006.01) |
| *A61F 5/01* | (2006.01) |

(52) U.S. Cl.
CPC .............. *A61F 13/00068* (2013.01); *A61F 5/01* (2013.01); *A61F 15/004* (2013.01); *A61F 2013/00272* (2013.01)

(58) Field of Classification Search
CPC ............ A61F 13/84; A61F 2013/8497; A61F 13/15747; A61F 13/55115; A61F 13/5511; A61F 13/5512; A61F 13/505; A61F 13/5622; A61F 13/471; A61F 13/49014; A61F 13/49413; A61F 13/15268; A61F 13/49; A61F 13/5203; A61F 13/551; A61F 13/49017; A61F 13/15; A61F 13/156; A61F 13/00068; A61F 15/004; A61F 5/01; A61F 13/041; A61F 15/002; A61F 15/008; A61B 12/006; A41B 13/10; A41D 13/04; A41D 13/08
USPC ........................ 602/3, 8, 20–22; 128/878–879
See application file for complete search history.

(56) References Cited

U.S. PATENT DOCUMENTS

| | | | | |
|---|---|---|---|---|
| 3,229,691 | A | * | 1/1966 | Crowe, Jr ........................... 602/1 |
| 5,176,669 | A | * | 1/1993 | Klemp ........................... 604/387 |
| 5,437,438 | A | * | 8/1995 | Takano et al. ............. 267/140.14 |
| 5,592,953 | A | * | 1/1997 | Delao ........................... 128/882 |
| 5,662,640 | A | * | 9/1997 | Daniels ........................... 604/392 |
| 5,817,038 | A | * | 10/1998 | Orange et al. ..................... 602/3 |
| 5,836,904 | A | | 11/1998 | Cooper |
| 6,520,926 | B2 | | 2/2003 | Hall |
| 7,347,848 | B2 | * | 3/2008 | Fernfors ........................ 604/392 |
| 8,142,378 | B2 | | 3/2012 | Reis |
| 2002/0115955 | A1 | | 8/2002 | DeSena |
| 2007/0134303 | A1 | | 6/2007 | Yahiaoui |

\* cited by examiner

*Primary Examiner* — Michael Brown
(74) *Attorney, Agent, or Firm* — Daniel Boudwin; Global Intellectual Property Agency LLC

(57) ABSTRACT

A protective wrap for a bandage or wound site is provided, wherein the wrap comprises a water impermeable and elastic material that shrouds a portion of a wearer's limb from moisture while showering. The device comprises an elongated wrap body having a pair of ends and an upper and lower edge. A first and second tie strap is disposed the wrap body and on the upper and lower edge, respectively. Along one end and along the interior surface of the wrap is a moisture absorbing material, while along a portion of the upper end is a second length of moisture absorbing material. The second length is also disposed on the interior surface and extends a portion or the substantial entirety of the upper edge length. The wearer places the wrap body around a limb and over an affected area, wherein the tie straps secure the wrap in place.

8 Claims, 3 Drawing Sheets

PROTECTIVE LIMB WRAP

CROSS REFERENCE TO RELATED APPLICATION

This application claims the benefit of U.S. Provisional Application No. 61/896,974 filed on Oct. 29, 2013. The above identified patent application is herein incorporated by reference in its entirety to provide continuity of disclosure.

BACKGROUND OF THE INVENTION

1. Field of the Invention

The present invention relates to a protective body wrap that facilitates a user taking a shower with an open wound, a cast, or similar sensitive area that cannot be exposed to moisture. More specifically, the present invention relates to a multi-layered body wrap having a moisture absorbing core and a water resistant outer layer to wrap different limbs and protect wound sites, bandages, or casts thereon.

It can be difficult for surgical patients with open wound sites or bandaged areas to bathe themselves without compromising the integrity of the bandage or contaminating the wound site. A common procedure for limb wounds is to leave the limb out of the shower area and bathe the rest of the body. This procedure can be effective, but is tiresome, inefficient, and tends to lead to water contacting the affected area anyway by accident and based on its proximity and exposed surface to the shower water.

Another common technique is to cover the affected limb using a plastic bag. This second technique is helpful but does not always ensure a moisture-tight seal around the limb, leading leakage and exposure to the shower water. This technique further often requires the use of securing tape or similar adhesive to secure the bag around the limb, whereafter the moistened cover is discarded. This is both messy and wasteful.

To prevent surgical patients and those with wound sites from endangering their wounds or compromising the bandage site, and to allow the user to take regular showers in the event of a limb injury, the present invention contemplates a new, reusable limb covering. The device comprises a bandage covering that is adapted to wrap around a limb and protect the affected area from moisture via an impermeable outer layer and a moisture absorbing inner layer. The device adapted to be placed over a user's skin and any underlying limb bandage. This allows patients to regularly shower and not have to resort to ad hoc methods of protecting these sensitive, post-injury or post-surgical sites on a limb.

2. Description of the Prior Art

Devices have been disclosed in the prior art that relate to bandage covers and wound wrappings. These include devices that have been patented and published in patent application publications, and generally relate to stabilizing splints or cast sleeves. The following is a list of devices deemed most relevant to the present disclosure, which are herein described for the purposes of highlighting and differentiating the unique aspects of the present invention, and further highlighting the drawbacks existing in the prior art.

One such device in the prior art is U.S. Pat. No. 8,142,378 to Reis, which discloses an immobilizing splint in the form of an inflatable wrap, whereby the device is inflatable to prevent movement of a patient's limb and is water-resistant to block moisture. Inflatable tubes are provided in the wrap that attached to a removable hand pump, whereby the device restricts movement of a limb when applied and inflated therearound. The intent of the Reis device is to provide a splint device that can be filled with air, as opposed to a hard cast or similar permanent immobilization device. While comprising a water-resistant material, the Reis device fails to provide end straps to secure the ends of the device to the wearer, and further fails to contemplate internal moisture absorbent material to absorb water that may bypass the wrapping. The present invention is contemplated as a temporary wrap that shields a limb or bandage from moisture while showering, whereby the device includes tethers that are used to secure the ends thereof adjacent to the affected area, and further wherein internal sponge elements are provide to wick moisture from the ends of the wrap in the event of moisture penetration.

U.S. Pat. No. 5,836,904 to Cooper discloses a comfort sleeve for a medical splint or cast, wherein the sleeve is adapted to provide a covering thereover that is padded and has improved aesthetics. The device comprises a fabric sleeve with a lining portion, a first open end, and a second open end with a thumb loop adjacent thereto. The device is elastic and comprises a soft interior layer, whereby end straps are contemplated for securing the device. However, the device of Cooper is not suited for use as a shower cover for a cast or wound site as provided herein. The device is an elastic, fabric material that is adapted to provide a cushioned outer surface for a cast or splint. The present invention comprises a substantially inelastic, plastic material that is water impermeable and includes an interior surface adorned with moisture absorbing elements therealong. The present invention is suited for use in the shower, while the Cooper device is contemplated for long-term use to cover a cast, for looks and for use in athletic competitions.

U.S. Pat. No. 6,520,926 to Hall discloses a compression support sleeve that is comprised of a thin polyurethane film coated with adhesive and sandwiched between an elastic, elastomeric polymer material. The polymer material is bonded to the adhesive surfaces of the film, and the assembly is utilized to form a cylindrical sleeve that supports limbs and joints of a wearer. The inner surface of the inner polymer material is adorned with a discontinuous layer of silicone microdots, which increase the friction coefficient of this surface such that the sleeve does not migrate away from its original position while in use. The Hall device describes a new and novel sleeve assembly that will resist movement while the wearer is in motion. The present invention, by contrast, is adapted to cover a portion of a limb or joint only when in the shower, whereby the device is secured using tethers along its open ends and is substantially inelastic.

The present invention comprises a limb wrap that is water impermeable and comprised of an elastic, elastomeric material that wraps around a wound site or bandage to protect the same from moisture while showering. The device includes the elastic wrap body, which acts as a moisture shell over an affected area. Also provided along the interior surface of the wrap body is a first and second strip of moisture absorbing or wicking material, which is adapted to absorb moisture that may seep beneath the wrap when donned. Securing the wrap in place is a first and second tie strap, which are elastic members along the upper and lower edges of the device to secure the wrap body in place after being wrapped over the wearer's limb.

The present invention prevents water from contacting a wound site or a bandage while a wearer is showing or bathing, whereby the device wraps around the outside of the area and around the wearer's limb. Its structure and intended use are substantially divergent in design from the prior art, and consequently it is clear that there is a need in the art for an improvement to existing wound site protective wrap devices. In this regard the instant invention substantially fulfills these needs.

SUMMARY OF THE INVENTION

In view of the foregoing disadvantages inherent in the known types of protective limb wraps now present in the prior art, the present invention provides a new wrap structure that can be utilized for providing convenience for the user when protective a wound site, bandaged area, or cast structure on a wearer's limb while showering.

It is therefore an object of the present invention to provide a new and improved protective limb wrap that has all of the advantages of the prior art and none of the disadvantages.

It is another object of the present invention to provide a protective limb wrap that shrouds wound sites and bandages from moisture without otherwise restricting a wearer while showering or bathing.

Another object of the present invention is to provide a protective limb wrap that comprises an elastic, elastomeric wrapping material that is water impermeable and stretches around the limb of a wearer when donned.

Yet another object of the present invention is to provide a protective limb wrap that includes a first and second strip of moisture absorbing material along the underside of the wrapping that absorbs moisture that penetrates the upper edge and exposed end of the wrap when donned.

Another object of the present invention is to provide a protective limb wrap that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
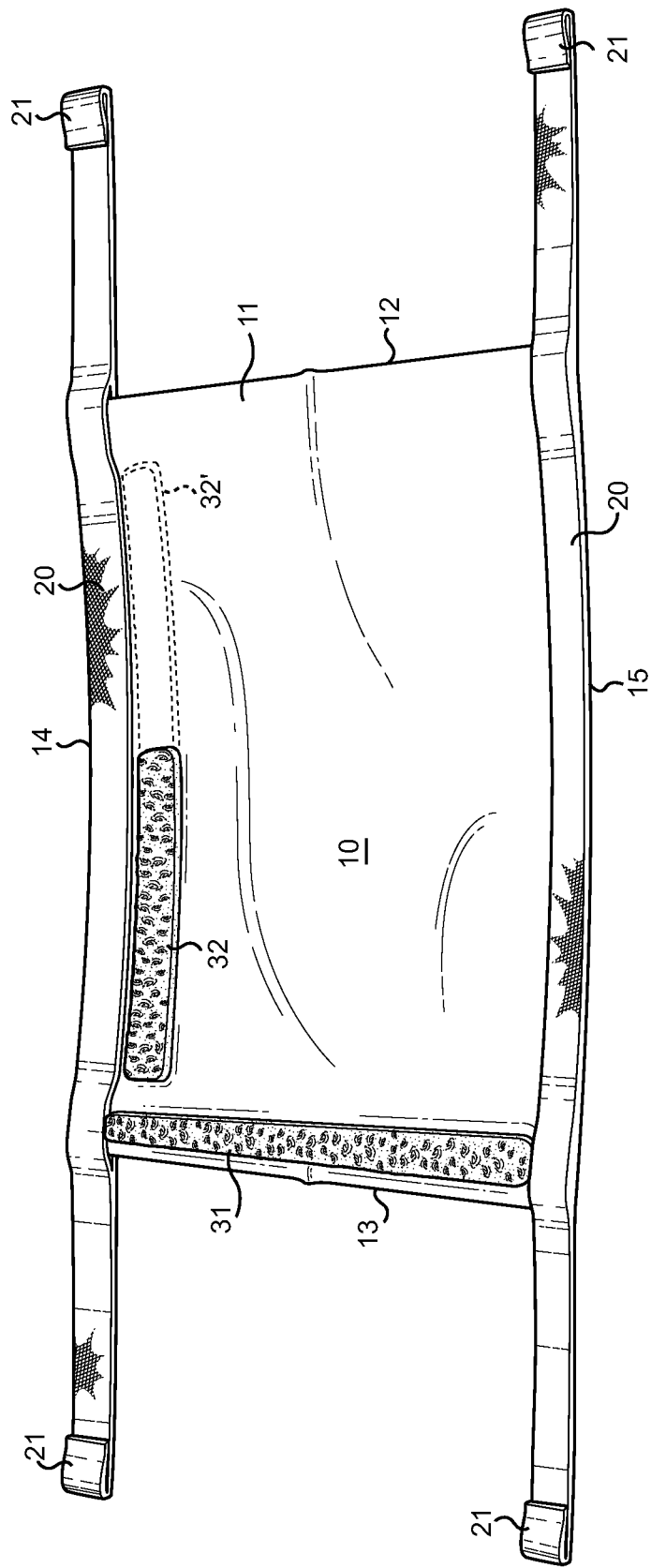
FIG. 1 shows the wrapping of the present invention in an open state, wherein the interior surface of the wrapping is exposed.

Reference is made herein to the attached drawings. Like reference numerals are used throughout the drawings to depict like or similar elements of the protective limb wrap of the present invention. For the purposes of presenting a brief and clear description of the present invention, the preferred embodiment will be discussed as used for protecting bandages or wound sites from moisture while a wearer is showering or bathing. The figures are intended for representative purposes only and should not be considered to be limiting in any respect.

Referring now to FIG. 1, there is shown a view of the protective wrapping of the present invention in an open state, wherein the interior surface 10 of the wrapping body 11 is shown. The protective wrapping of the present invention comprises a wrapping body 11 that has an elongated length and a material that is moisture impermeable and elastic in structure. The body 11 comprises a thin layer plastic sheet or elastomeric material that is inherently elastic, whereby the body 11 of the wrapping can be wrapped around a limb and drawn tightly over a wound or bandage site. The body 11 comprises an upper 14 and lower 15 edge, and a first 13 and second 12 end. The upper and lower edges form the major edges, while the ends are preferably shorter in length than the upper and lower edges. The wrapping body 11 is placed over a wound site or bandage and wrapped therearound, whereby the upper edge 14 is adapted to be positioned above the affected area on the wearer's limb, and the ends 11, 13 are wrapped circumferentially around the limb to shroud the area from moisture while showering or bathing.

Disposed on the upper 14 and lower 15 edges of the protective wrapping is a tie strap 20. The tie strap 20 is an elastic member, preferably plastic polymer or elastomeric material that stretches under load. The tie strap 20 extends the length of the upper 14 and lower 15 edges of the wrapping and extends outward therefrom. The ends 21 of the straps extend away from end the ends 11, 13 of the wrapping such that a length of the straps 20 is exposed along the ends. This allows the wearer to use the straps 20 as securing means, whereby the ends 21 are knotted together after being drawn together around the wearer's limb. The elasticity of the straps assists creating a waterproof seal along the upper 14 and lower 15 edges of the wrapping, whereby the user can draw the tie strap ends 21 together and into a knot to prevent water from entering underneath the wrapping body 11.

Along the interior surface 10 of the wrapping body 11 is disposed a first 31 and second 32 strip of moisture absorbing material. The moisture absorbing material comprises a sponge material or similar moisture absorbing or moisture wicking material. The first strip 31 is disposed along the first end 13 of the wrapping body 11 and substantially parallel thereto. The first strip 31 extend substantially then entire length of the first end 13 and is adapted to be sandwiched between the first end 13 and the second end 12 when the body 11 is wrapped around a wearer's limb. This prevents moisture leakage between the layers, which may otherwise cause the affected area on the wearer's limb to be exposed to soap and water.

The second strip 32 along the interior surface 10 of the wrapping body is positioned adjacent to the upper edge 14 and extends a portion of the length thereof. The second strip 32 extends only partially along the upper edge 14 or alternatively extends substantially the entire length (see 32'). The second strip 32, 32' is adapted to absorb moisture entering between the upper edge 14 of the wrapping and the user's skin above the affected area. The upper edge 14 is positioned above the affected area along the wearer's limb, whereby the second strip 32, 32' provides a barrier for moisture that may find its way beneath the wrapping. The tie straps 20 are drawn together such that water penetration is held to a minimum, while the first and second strips 31, 32, 32' provide insurance against any potential leaks. When in place, the wrapping body 11 prevents direct contact of water with an affected area on the wearer's limb.

Figure 2:
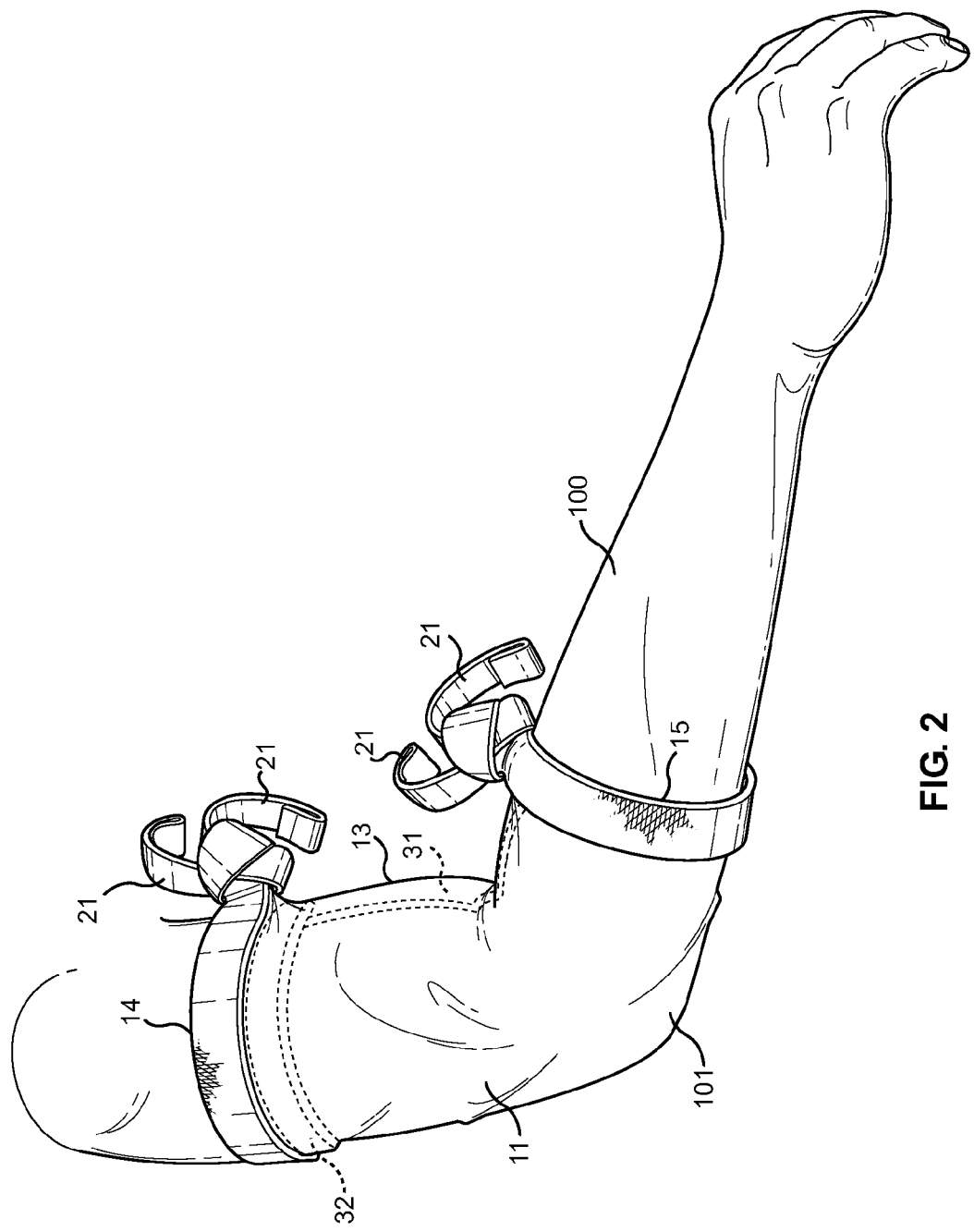
FIG. 2 shows the wrapping donned around the arm of the wearer, wherein the elastic structure accommodates movement of joints while protecting underlying areas from moisture.

Referring now to FIG. 2, there is shown a view of the protective wrapping of the present invention in a working state, positioned around the limb 100 of a wearer and providing coverage over an affected area. The body 11 of the wrapping is positioned around the circumference of the limb 100, wherein the first end 13 is positioned over the second end and the upper edge 14 is positioned higher on the limb 100 than the lower edge 15. The tie strap ends 21 are tied together, drawing the upper 14 and lower 15 edges of the wrapping together and bearing the wrapping against the user's skin.

When donned, the second moisture absorbing strip 32 is positioned above the affected area, whereby any water on the user's skin that may pool or cascade downward along the limb is absorbed thereby. This prevents moisture from entering between the upper edge 14 and the user's skin by way of gravity. Similarly, the first moisture absorbing strip 31 along the first end 31 is positioned against the outer surface of the wrapping body and sandwiched between the first end 31 and the outer surface. This prevents water penetration through this line of connection. The outer surface of the moisture absorbing material may further comprise a tacky material, thereby creating a tacky outer surface that affixes the strips 32, 31 to the user's skin and wrapping body outer surface, respectively. This further prevents separation along the length of the wrapping first end 13 when the wrapping is positioned over a limb joint 101.

The wrapping body 11 is a thin film, elastic material that preferably comprises a plastic material or similar elastomeric material that is water impermeable. The elasticity of the wrapping allows the wearer to tightly secure the wrapping over a wound or bandage, whereby the wrapping body 11 is stretched and secure fitment is ensured. The moisture absorbing strips 31, 32 are preferably a foam or sponge material that absorb a quantity of moisture and retain the same. These strips are the final line of moisture defense after the tie straps secure the ends and edges of the device. The elasticity prevents the wrapping from being a loose-fitting cover, which is the primary means of preventing moisture penetration. The tie straps are also preferably an elastic material, whereby the straps can be stretched and tied together when deploying the wrap over a limb. Once the device has been deployed a first time, it can be discarded or dried for subsequent re-use.

Figure 3:
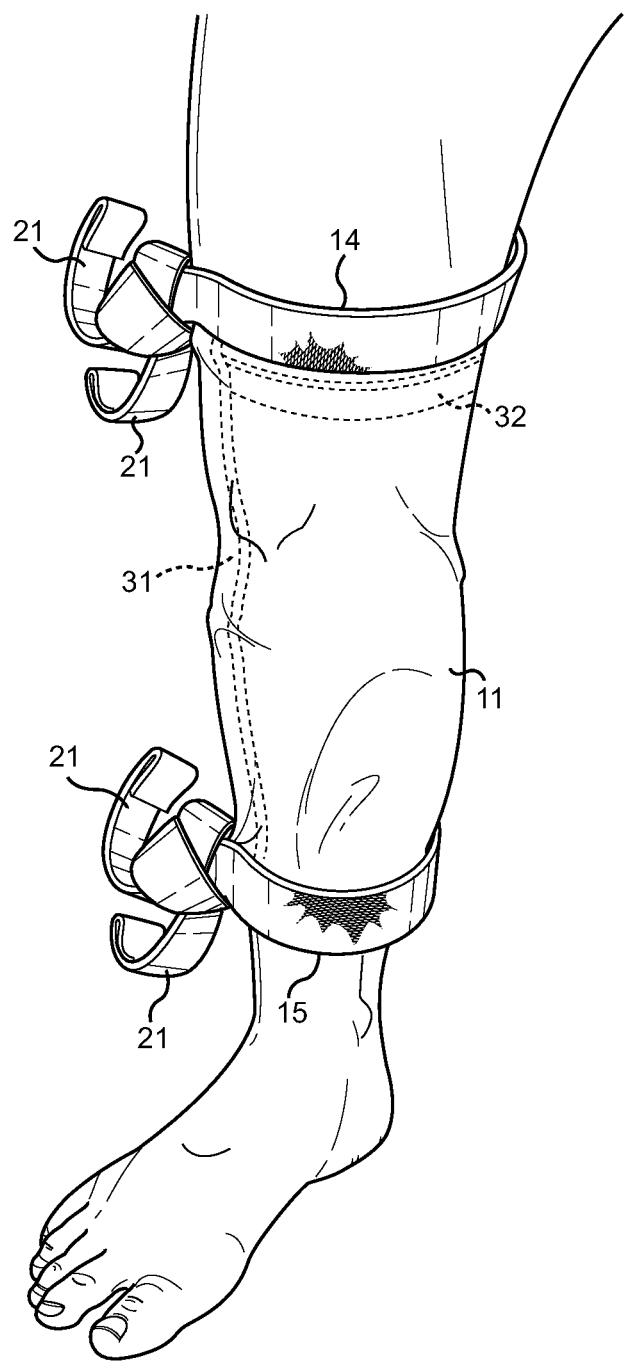
FIG. 3 shows another view of the wrapping donned on the limb of a wearer for protecting the underlying area from moisture.

Referring now to FIG. 3, there is shown a view of the present invention donned on yet another limb of a wearer. As shown the body 11 of the wrapping is stretched over and around the limb, whereby the underlying area is protected from moisture as the user bathes or showers. The first 31 and second 32 moisture absorbing strips seal the first end and the upper edge 14 of the wrapping, while the tie strap ends 21 are used to secure the assembly against the wearer's body. The inherent elasticity of the body material and the straps allows the device to form a covering over a limb or joint that can flex with the wearer. The material expands and contracts with limb movement or joint flexure while maintaining a secure fitment thereagainst. The tie straps secure the upper 14 and lower edges 15 of the wrapping to the wearer's limb to prevent sliding of the assembly and to ensure the ends stay abutted against the user's skin during limb movements. Finally, the optional tacky outer surface of the moisture absorbing strips further assist in sealing the wrapping once positioned over an affected area.

It can be difficult for surgical patients and those with bandages or casts to protect their wounds from soap and water when showering or bathing. Some patients may wrap their wounded limb in a plastic bag, but this can be uncomfortable and inconvenient. Casts, bandages and wound sites must be protected at all times, and moisture represents a threat to the wound site and the medical coverings thereover. Therefore efficient and secure shrouding of these areas is necessary to allow a patient to clean themselves during the healing process. The present invention is submitted as a means to shroud and protect an affected area such as this on the limb of a patient. The device comprises a protective wrap that can surround and secure against an arm or leg of a user. The device includes a water impermeable and elastic layer, moisture absorbing interior strips, and elastic straps used to secure the assembly. The present invention protects surgical sites and bandages from moisture when showering or bathing, thereby providing patients with peace of mind after their operation or injury while showering that their wound will not become infected and the medical bandages deployed will not be compromised.

It is submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A protective wrapping for the limb of a wearer, comprising:
   an elongated wrapping body comprising a thin layer, elastic and water impermeable material;
   said wrapping body having a first end, a second end, an upper edge, a lower edge, and an interior surface;
   a first tie strap disposed along said upper edge and extending outward from said first end and said second end and terminating at a pair of upper tie strap ends;
   a second tie strap disposed along said lower edge and extending outward from said first end and said second end and terminating at a pair of lower tie strap ends;
   a first strip of moisture absorbing material disposed on said interior surface and along said first end;
   a second strip of moisture absorbing material disposed on said interior surface and along said upper edge;
   said first strip and said second strip of moisture absorbing material adapted to absorb moisture when in contact therewith;
   said elongated wrapping body adapted to wrap around the limb of a wearer and stretch therearound to establish a water impermeable layer thereover;
   said upper tie strap ends adapted to be tied together;
   said lower tie strap ends adapted to be tied together.

2. The protective wrapping of claim 1, wherein:
   said second strip of moisture absorbing material extends partially along the length of said upper edge.

3. The protective wrapping of claim 1, wherein:
   said second strip of moisture absorbing material extends substantially along the entire length of said upper edge.

4. The protective wrapping of claim 1, wherein said first tie strap and said second tie strap are comprised of an elastic material.

5. The protective wrapping of claim 1, wherein:
   said first strip of moisture absorbing material further comprises an interior surface;
   said interior surface of said first strip further comprising a tacky surface.

6. The protective wrapping of claim 1, wherein:
   said second strip of moisture absorbing material further comprises an interior surface;
   said interior surface of said second strip further comprising a tacky surface.

7. The protective wrapping of claim 1, wherein said elongated wrapping body further comprises an elastic polymer material.

8. The protective wrapping of claim 1, wherein said elongated wrapping body further comprises an elastomeric material.

\* \* \* \* \*